United States Patent
Parsons

[19]

[11] Patent Number: 6,056,763

[45] Date of Patent: May 2, 2000

[54] TONGUE SCRAPER

[76] Inventor: Lorna Parsons, P.O. Box 793, Pine Lake, Ga. 30072

[21] Appl. No.: 09/195,027

[22] Filed: Nov. 18, 1998

[51] Int. Cl.[7] .................................................. A61B 17/24
[52] U.S. Cl. ......................... 606/161; 606/160; 606/131; 15/111
[58] Field of Search ..................................... 606/161, 160, 606/162, 131; D24/146, 147, 149, 136, 176, 152; 15/111, 193.1, 110

[56] References Cited

U.S. PATENT DOCUMENTS

| | | | |
|---|---|---|---|
| 3,683,924 | 8/1972 | Louie | 128/304 |
| 4,582,059 | 4/1986 | Tiwari | 128/304 |
| 5,217,475 | 6/1993 | Kuber | 606/161 |
| 5,282,814 | 2/1994 | Srivastava | 606/161 |
| 5,569,278 | 10/1996 | Persad | 606/161 |
| 5,735,864 | 4/1998 | Heising, Jr. | 606/161 |

*Primary Examiner*—Michael Buiz
*Assistant Examiner*—Lien Ngo
*Attorney, Agent, or Firm*—Joseph N. Breaux

[57] ABSTRACT

A tongue scraper system comprising a handle having a pair of forks extending from a distal end of the handle wherein the forks are constructed of resilient flexible material with a spring loaded notched adjuster provided between the two forks which allows a user to adjust spacing between the distal ends of the forks. A blade notch is provided in the distal ends of each fork while a plastic or metal flexible tongue scraping blade is designed to be held in a curved configuration by the fork ends. A sure grip extended handle provides easy gripping.

5 Claims, 2 Drawing Sheets

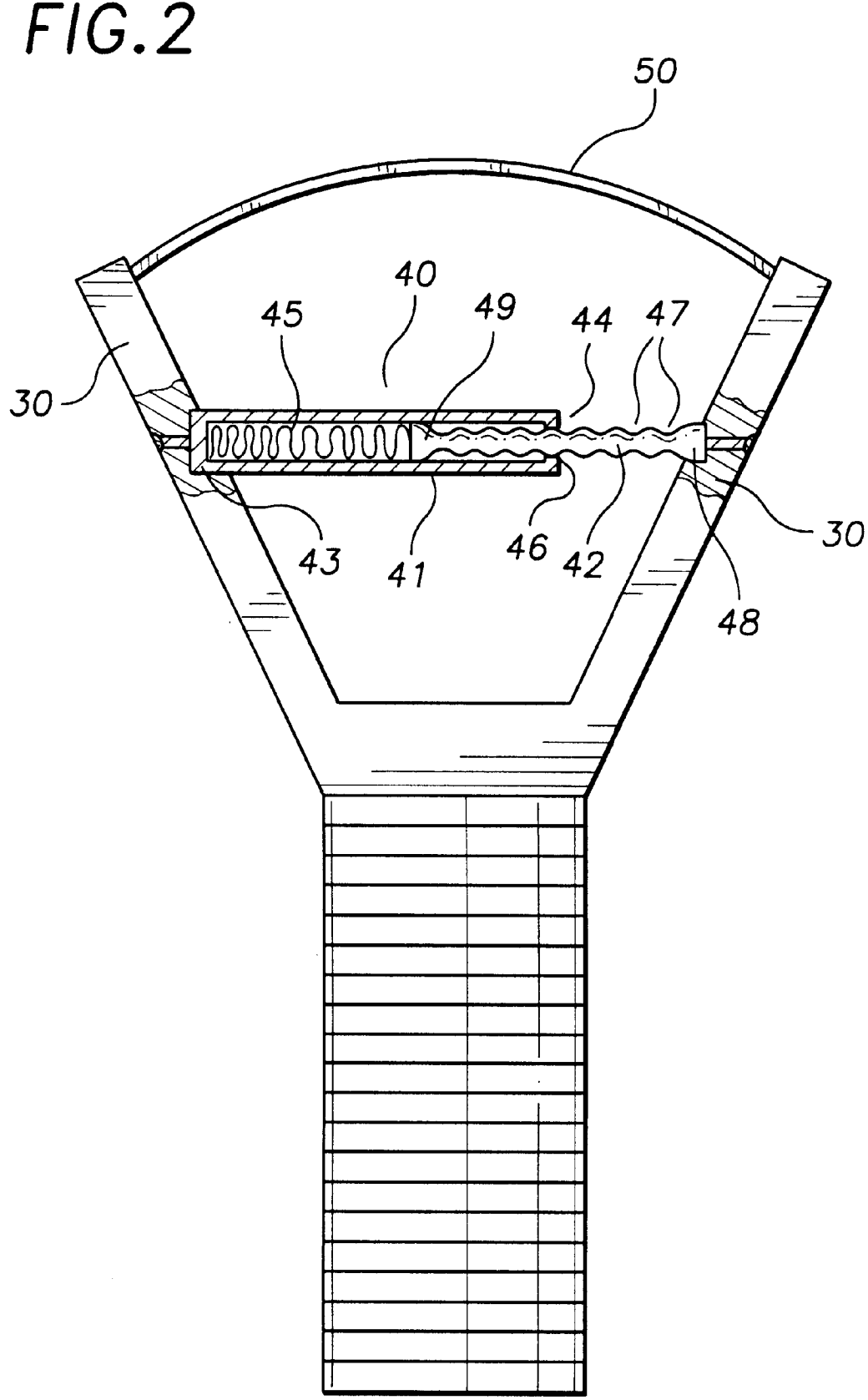

TONGUE SCRAPER

TECHNICAL FIELD

The present invention relates to devices and methods for tongue scrapers and more particularly to devices and methods for a tongue scraper comprising a handle having a pair of forks constructed of resilient flexible material extending from one side edge thereof wherein a spring loaded notched adjuster is provided between the two forks allowing a user to adjust spacing between distal ends of the forks, each of the distal ends of the forks is provided with a blade notch and a released button for holding a plastic or metal tongue scraping blade that is designed to be held in a curve configuration for use.

BACKGROUND ART

There has been numerous tongue scraper designs patented many of which include scraping devices which have blades that are replaceable and may or may not include serrated edges. Some of the prior art scrapers include handles with extensions, and may include replaceable antiseptic pads. Although these prior art devices are useful for their stated purposes there has never been a tongue scraper device as the present which has a low profile to prevent gagging by the user, includes an adjustable width tongue scraper device which allows the tongue scraper to be adjusted for a user's mouth width, and includes a handle for easy reaching by the user. The unique elements of the present invention provide a tongue scraper which overcomes numerous problems not previously recognized by those in the art and while also providing a simple to manufacture and cost effective dental hygiene apparatus.

The prior art patents which are relevant are as follows:

Heisinger, Jr., U.S. Pat. No. 5,735,864; Persad, U.S. Pat. No. 5,569,278; Srivastava, U.S. Pat. No. 5,282,814; Kuber, U.S. Pat. No. 5,217,475; Tiwari, U.S. Pat. No. 4,582,059; and Louie, U.S. Pat. No. 3,683,924.

As will be shown below, the present invention provides a unique dental hygiene apparatus which is easy to use and comfortable. The device is a low profile adjustable tongue scraping device with an adjustable and removable tongue scraping blade with an extended handle. As known by those skilled in the art proper oral hygiene is necessary to prevent halitosis. Urging persons to practice proper oral hygiene is greatly facilitated if proper tools are available which are not only effective but easy to use. The present device provides a tool which motivates persons to conduct oral hygiene practices more often by providing a tool that allows a user to scrape ones tongue without gagging and also a tool which has width adjustable extension members that adjustably bend the flexible removable blade to adapt the blade width to a user's mouth width, the device includes an extendable handle for easily reaching the back portions of a person's tongue.

GENERAL SUMMARY DISCUSSION OF INVENTION

It is thus an object of the invention to provide a tongue scraper that is adjustable to be adapted for use by any width mouth and tongue.

It is a further object of the invention to provide a tongue scraper that has a low profile design which prevents gagging when used.

It is a still further object of the invention to provide a tongue scraper that comprises a handle having a pair of resilient forks extending from a handle with a tongue scraping blade attached to distal ends of the forks while the distance between the distal ends of the forks is adjusted using a spring loaded notching device placed between the forks thereby allowing the width of the scraper blade to be adjusted to suit a width of a person's tongue.

Accordingly, a tongue scraper is provided that comprises a handle having a pair of forks constructed of a resilient flexible material which extends from one side edge of the handle and wherein a spring loaded notching and positioning adjuster is placed between the two forks and allows a user to adjust spacing distance between distal ends of the forks, each of the distal ends of the fork is provided with a blade mounting notch and a blade release button for holding a flexible plastic or metal tongue scraping blade that is designed to be held in a curved configuration for use.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 2 is a top plane view of the spring loaded adjuster placed between the two forks illustrating the curved blade placed therein.

EXEMPLARY MODE FOR CARRYING OUT THE INVENTION

Figure 1:
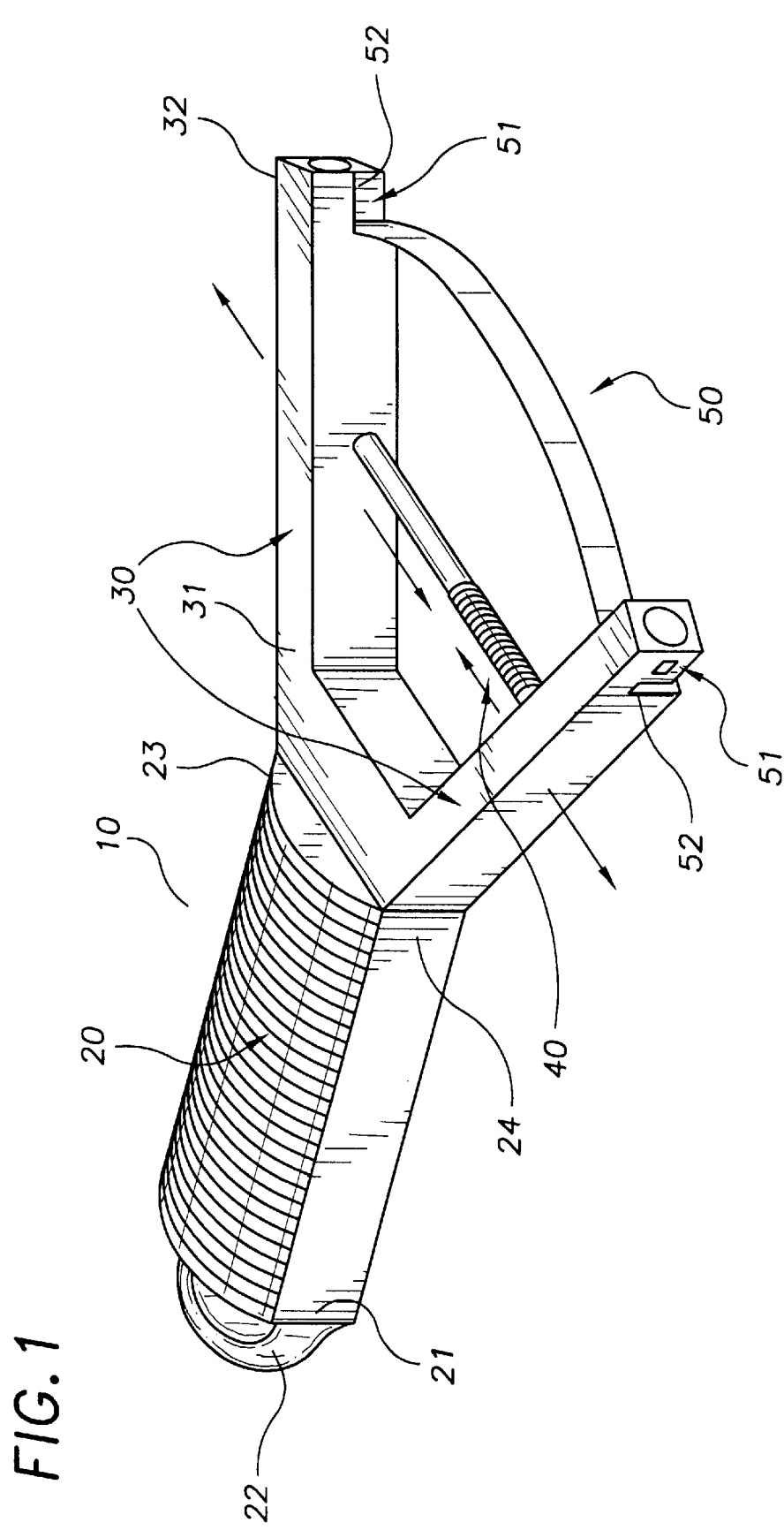
FIG. 1 is an isometric view of the tongue scraper illustrating its component parts.

It can be seen from the following description that in use a person desiring to scrape his/her tongue would adjust the tongue scraper fork distal ends by utilizing the notched spring loaded adjustment positioned between the forks. It is preferable to adjust the fork distance to suit the particular dimension of the user's mouth and is more readily done so while a user makes incremental adjustments of the notched adjuster as necessary for comfort. The device is inserted into a mouth and the scraper placed on the top back portion of the tongue and then drawn out of the mouth slowly to scrape the upper surface of the tongue. Upon completion the user would then rinse the scraper blade under hot running water. When the blade becomes worn or broken for any reason it is replaceable by snapping the ends of the blade into the distal ends of the fork extension.

Referring to the figures in detail, FIG. 1 illustrates to the tongue scraper 10 which includes a handle component 20, two fork extensions 30, a spring loaded notched fork width adjustment 40 and a resilient tongue scraping blade 50.

The handle 20 is preferably constructed of a rubber coated plastic which provides comfort and easy gripping by the user. A proximal end 21 of the handle includes a looped portion 22 for hanging the scraper when not in use. A distal end 23 of the handle includes the attachment of the forks members 30. The fork members 30 are attached to side edges 24 of the distal end of the handle 23 and extend to form resilient flexible members which extend about two to about four inches from the distal end of the handle 23. The forks include a proximal end 31 which is attached to the distal end of the handle 23 and distal end 32 which is used to mount the flexible scraper blade 50. The scraper handle and forks are preferably constructed as a unit in one piece while the plastic material used to construct the device would be a plastic suitable for molding and which would provide resiliency as required by the fork members.

FIG. 2 illustrates the spring loaded notched fork width adjustment 40 in detail which includes a female cylindrical member 41 which receives an elongated male notched piston 42. The female cylindrical member 41 includes an end 43 which is fixedly secured to an inside edge of one of the fork members 30 and an open end 44 which receives the male member 42. A spring 45 is placed within the cylinder and urges the male portion to move out of the cylinder. The open end of the cylindrical member 44 includes a protruding perimeter inner edge 46 which engages with the notched male member 42. The male member 42 includes numerous evenly spaced circumferential notches 47 each of which may be engaged with the protruding perimeter inner edge 46. One end of the male notched member 48 is fixedly secured to the other fork member 30 while the other end of the notched male member 49 is inserted into the female cylindrical member 41. The fork width adjuster 40 provides a means for incrementally adjusting the distance between the two fork members. The user would grasp the two fork members between his/her fingers and squeeze the fork members together which pushes the male member 42 into the female cylindrical member and incrementally engages and disengages the numerous notches of the male member with the protruding perimeter inner edge until the user has the fork members at a desired distance apart. The fork members are held in position by the resilient engagement of the perimeter protruding inner edge with one of the numerous circumferential notches on the male member. The width adjustment allows the tongue scraper device to be altered in width so that the tongue scraping blade may be adjusted to fit the mouth dimensions of the particular user.

The blade 50 is preferably constructed of resilient and flexible material which may include stainless steel, plastic or other material particularly suited for such application. The ends of the blade 51 include a knob portion which is received by a keyed receiving notch 52. The keyed receiving notch 52 lockingly engages the blade on each fork member end and further prevents the blade from being removed from the fork member end during normal operational use of the tongue scraper. The scraper blade 50 is preferably of a length which requires it to be arched in order to be installed in the fork ends. The arched orientation provides a natural shape to fit the contour of a user's tongue upper surface. Additionally, as the user incrementally adjusts the fork end adjustment means the arch of the blade is substantially increased. The blade may also be provided with serrations or other edge configurations to help assist the user in scraping his/her upper tongue surface.

The handle member 20 also includes a rubber gripping portion which is preferably contoured to fit the natural grip of a human thereby providing a comfortable handle for use of the tongue scraper.

It is noted that the embodiment of the tongue scraper described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A tongue scraper comprising:

a) a handle portion configured to be gripped by a user in one hand with a proximal end and a distal end while the handle includes two side edges extending a length of the handle, b) two resilient fork members attached to the distal end of the handle and extending parallel to each other and from the side edges of the handle, the fork members each having a distal end and a proximal end with a blade engagement groove formed in the proximal end of each fork member, c) a spring loaded notched adjuster positioned between the two fork members and about midway between the proximal and distal ends of the fork members which provides a means for incrementally adjusting the distance between the two fork members, the notched adjuster comprises: an elongated female cylinder with an open end and a closed end fixedly mounted to an inside edge of one of the fork members with a spring positioned in an interior of the cylinder and wherein the cylinder opening includes a protruding perimeter inner edge; a notched male elongated piston dimensioned to be received by the cylinder opening wherein the notched male elongated piston includes numerous evenly spaced circumferential notches with one end fixedly mounted to an inside edge of the other fork member and the other end received by the female cylinder while the protruding perimeter inner edge of the female cylinder is resiliently engaged by one of the numerous evenly spaced notches and wherein the protruding perimeter edge and the numerous evenly spaced circumferentially spaced notches are dimension so that when a user urges the two fork members together and overcomes the resilient engagement of the protruding perimeter inner edge and one of the numerous evenly spaced notched and the spring the male piston is pushed into the female cylinder thereby positioning the fork members closer together, and d) a flexible tongue scrapper blade with mounting ends received by the blade engagement grooves on each of the fork member distal ends, the blade is of a length so that in order to mount on the fork distal ends the blade must be forced in an arched orientation.

2. The tongue scraper of claim 1, wherein the handle portion further comprises a hooked member attached to a proximal end of the handle which provides a means for storing the tongue scraper.

3. The tongue scraper of claim 1, wherein the handle portion further comprises a rubber hand grip portion extending around the handle and formed to contour to a grip of a user.

4. The tongue scraper of claim 1 wherein the blade further comprises an engagement knob one each end of the blade and which knob is received by a keyed receiving notch on the end of each fork member.

5. The tongue scraper of claim 1 wherein the blade further comprises a serrated blade edge which assist a user in effectively scraping his or her tongue upper surface.

* * * * *